United States Patent
Tu et al.

(10) Patent No.: US 9,605,109 B1
(45) Date of Patent: Mar. 28, 2017

(54) PHOSPHOROUS CONTAINING COMPOUNDS AND PROCESS FOR SYNTHESIS

(71) Applicant: Chang Chun Plastics Co. Ltd., Taipei (TW)

(72) Inventors: An-Pang Tu, Taipei (TW); Szu-Fang Chen, Taipei (TW); Ping-Chieh Wang, Taipei (TW); Kuen-Yuan Hwang, Taipei (TW)

(73) Assignee: Chang Chun Plastics Co. Ltd., Taipei (TW)

( * ) Notice: Subject to any disclaimer, the term of this patent is extended or adjusted under 35 U.S.C. 154(b) by 0 days.

(21) Appl. No.: 15/066,745

(22) Filed: Mar. 10, 2016

Related U.S. Application Data

(62) Division of application No. 14/932,092, filed on Nov. 4, 2015.

(51) Int. Cl.
| | |
|---|---|
| C08G 79/02 | (2016.01) |
| C07F 9/02 | (2006.01) |
| C08G 59/30 | (2006.01) |
| C07F 9/6571 | (2006.01) |
| C08G 59/42 | (2006.01) |
| C09K 21/14 | (2006.01) |
| C09K 21/12 | (2006.01) |
| C08J 5/24 | (2006.01) |
| C08J 5/04 | (2006.01) |

(52) U.S. Cl.
CPC ...... *C08G 59/304* (2013.01); *C07F 9/657163* (2013.01); *C08G 59/423* (2013.01); *C08J 5/043* (2013.01); *C08J 5/24* (2013.01); *C09K 21/12* (2013.01); *C09K 21/14* (2013.01); *C08J 2363/00* (2013.01); *C08J 2363/02* (2013.01)

(58) Field of Classification Search
CPC .. C08K 5/5313; C08G 59/304; C08G 59/423; C07F 9/657163; C09K 21/14; C09K 21/12; C08J 5/043; C08J 5/24; C08J 2363/00; C08J 2363/02
USPC ......... 523/451; 528/398; 558/82; 568/12, 14
See application file for complete search history.

(56) References Cited

U.S. PATENT DOCUMENTS

| | | | |
|---|---|---|---|
| 6,441,067 B1 | 8/2002 | Chiu et al. | |
| 6,984,716 B2 | 1/2006 | Hwang et al. | |
| 7,064,157 B2 | 6/2006 | Hwang et al. | |
| 8,134,021 B2 | 3/2012 | Lin et al. | |
| 8,426,547 B2 | 4/2013 | Su et al. | |
| 2004/0077821 A1 | 4/2004 | Hwang et al. | |
| 2010/0004426 A1* | 1/2010 | Lin | C07F 9/657172 528/399 |
| 2014/0072818 A1 | 3/2014 | Zeng et al. | |

FOREIGN PATENT DOCUMENTS

| | | |
|---|---|---|
| CN | 102850722 A | 1/2013 |
| CN | 103626958 A | 3/2014 |
| TW | 523526 B | 3/2003 |
| TW | I322810 B | 4/2010 |
| TW | I351406 B | 11/2011 |
| TW | I359152 B | 3/2012 |

* cited by examiner

*Primary Examiner* — David Karst
(74) *Attorney, Agent, or Firm* — Polsinelli PC

(57) ABSTRACT

The instant disclosure relates to phosphorus-containing compounds that can be used to form flame retardant phosphorus-containing resins, and also can serve as a hardener for a flame retardant epoxy resin compositions. In particular, the phosphorus-containing compounds are modified with acyloxy groups (—O—(C═O)—R), as shown below. Incorporation of the acyloxy groups results in resins that are water resistant and exhibit improved dielectric properties.

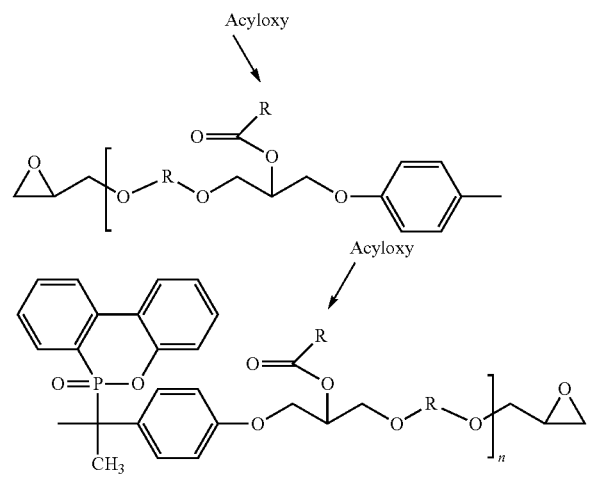

16 Claims, No Drawings

PHOSPHOROUS CONTAINING COMPOUNDS AND PROCESS FOR SYNTHESIS

CROSS REFERENCE TO RELATED APPLICATIONS

This application is a divisional of U.S. application Ser. No. 14/932,092, filed Nov. 4, 2015; the disclosure of which is incorporated herein by reference in its entirety.

FIELD OF THE DISCLOSURE

The present disclosure relates to phosphorus-containing compounds and preparation methods thereof, and more particularly, to phosphorus-containing compounds which can directly react to form phosphorus-containing epoxy resin or serve as a hardener for an epoxy resin composition.

BACKGROUND

Due to good resistance to solvents, excellent mechanical strength, and electrically insulating properties, etc., epoxy resin is widely used. For example, epoxy resins are often applied to coating materials, electrically insulating materials, printed circuit laminated boards and electronic packaging materials, construction and building materials, adhesives, and navigation technology. Epoxy resins, however, can have poor thermal resistance and burn easily, which may set significant restriction on the uses of epoxy resin. Therefore, with development of electronic technology, the industry has sought to improve flame retardant properties and thermal resistance of epoxy resins.

There has been a plurality of techniques available for improving the flame retardant properties of epoxy resins, the most common one of which is to introduce a flame retardant into an epoxy resin compound. Often, a halogen-containing flame retardant is used. Although halogens are effective for retarding flames, they can produce erosive and toxic hydrogen halide gases.

Phosphorus-containing flame retardants have significant advantages of low toxicity, good processing properties, low usage amounts, and good compatibility with resins. During the burning process of the phosphorus-containing flame retardants, on the one hand, polymeric materials are urged to undergo a dehydration reaction by which hydrogen of carbohydrate reacts with oxygen of air to form water so as to reduce an ambient temperature and thereby provide a flame retardant effect. On the other hand, phosphoric acid is decomposed under a high temperature, making polymeric compounds carbonized to form a flame retardant coke layer; moreover, phosphoric acid would be further dehydrated and esterified under the high temperature to form glass-like melted polymeric phosphoric acid that covers surfaces of burning substances and serves as a protective layer for preventing oxygen from entering into non-burning internal portions of polymers and for impeding release of volatile decomposed substances, thereby inhibiting proliferation of flames and achieving the flame retardant effect.

Currently used phosphorus-containing substances can be divided into reactive phosphorus-containing compounds with function groups, and generally non-reactive phosphorus-containing compounds. The non-reactive phosphorus-containing compounds have relatively poor thermal resistance and are not suitably applied to epoxy resin compositions required to be highly thermal resistant. The reactive phosphorus-containing compounds bonded to other molecules can thus have relatively higher thermal stability and thereby become a mainstream of usage.

Among available reactive phosphorus-containing compounds, the most commonly used is a linear phosphorus-containing compound; however, due to an —O—P—O— bond on a main chain thereof, this linear phosphorus-containing compound has poorer thermal resistance than a normal halogen-containing or halogen-free epoxy resin composition. In another aspect, phosphorus-containing flame retardant resin compositions, no matter having linear phosphorus-containing compounds or non-reactive phosphorus-containing compounds, are worse in processing properties than bromine-containing epoxy resin compositions in practical applications. Therefore, it is deemed hard to enhance both the flame retardant properties and thermal resistance of the resin compositions.

SUMMARY OF THE DISCLOSURE

The instant disclosure relates to phosphorus-containing compounds that can be used to form flame retardant phosphorus-containing resins, and also can serve as a hardener for a flame retardant epoxy resin compositions. The instant disclosure also provides methods for preparing the phosphorus-containing compounds, resinous composition comprising the phosphorus-containing compounds, and flame retardants comprising the phosphorus-containing compounds.

9,10-dihydro-9-oxa-10-phosphaphenanthrene-10-oxide (DOPO) or 6-(1,1-bis(4-hydroxyphenyl)ethyl)dibenzo[c,e][1,2]oxaphosphinine 6-oxide (DMP) can be reacted with an epoxy to synthesize a phosphorous-containing epoxy, as shown below for DMP.

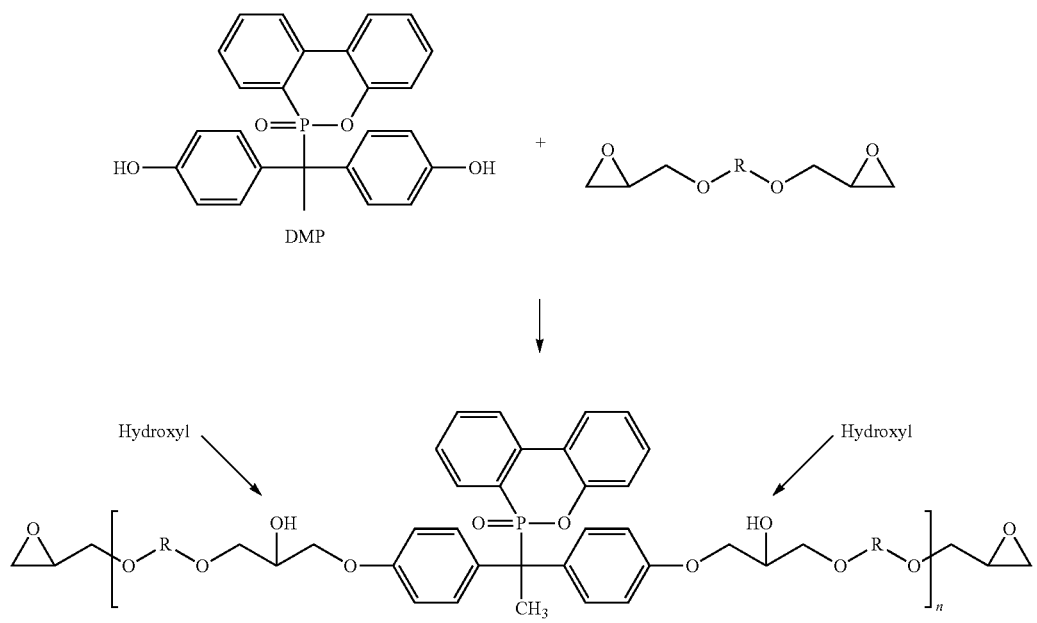

The "hydroxyl" groups on the DOPO and DMP, however, appear in the phosphorous-containing epoxy (as shown by the arrows) and result in a huge polarity in the molecule which contributes to high water absorption and inferior dielectric properties. To prevent the "hydroxyl" groups from forming in the phosphorous-containing epoxy, the hydroxyl groups on the starting material can be acylated so that the "hydroxyl" group is converted to an acyloxy group (—O—(C=O)—R). This results in less water absorption and better dielectric properties.

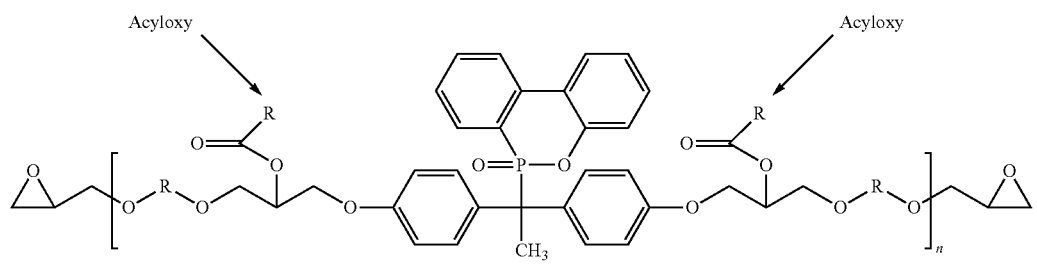

Therefore, in general, the instant disclosure relates to a compound of formula (I):

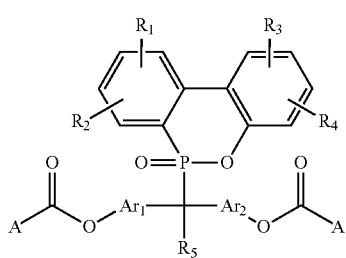

Formula (I)

wherein, $R_1$, $R_2$, $R_3$, and $R_4$ are independently selected from the group consisting of H, $C_1$-$C_{10}$, $C_1$-$C_{10}$ alkoxy, and $C_3$-$C_{10}$ cycloalkyl;

$R_5$ is independently selected from the group consisting of H, $C_1$-$C_{10}$ alkyl, $C_1$-$C_{10}$ alkoxy, $C_3$-$C_{10}$ cycloalkyl, and $Ar_3$; and $Ar_1$, $Ar_2$, and $Ar_3$ are independently selected from the group consisting of

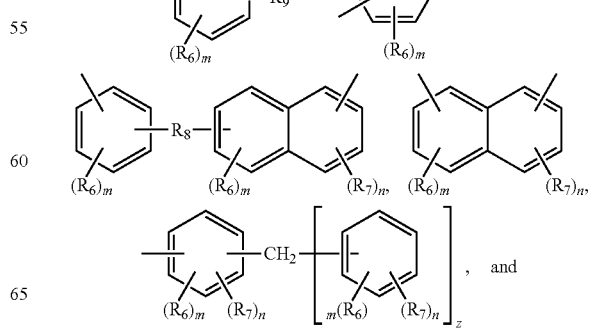

, and

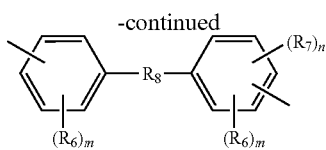

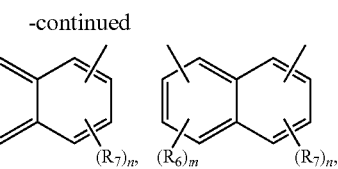

$R_6$ and $R_7$ are independently selected from the group consisting of H, $C_1$-$C_{10}$ alkyl group, $C_1$-$C_{10}$ alkoxy, and a cyclic alkyl group having 3-10 carbon atoms, M and n are independently an integer from 0 to 4;

$R_8$ is absent or is selected from the group consisting of —$CH_2$—, —$(CH_3)_2C$—), —$CO$—, —$SO_2$—, and —$O$—

$R_9$ is absent or is —$(CH_2)_p$, wherein p is an integer from 1 to 20;

A is selected from the group consisting of $C_1$-$C_{10}$ alkyl,

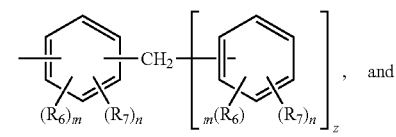

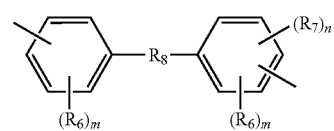

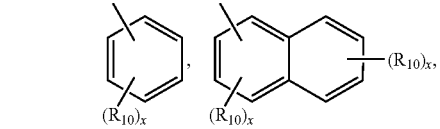

wherein, each $R_{10}$ is independently H or $C_1$-$C_{10}$ alkyl; and x is an integer from 0 to 4.

The instant disclosure relates to a compound of Formula (II):

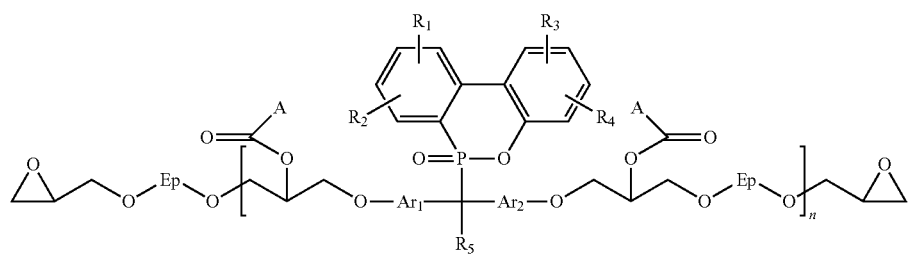

Formula (II)

wherein, $R_1$, $R_2$, $R_3$, and $R_4$ are independently selected from the group consisting of H, $C_1$-$C_{10}$, $C_1$-$C_{10}$ alkoxy, and $C_3$-$C_{10}$ cycloalkyl;

$R_5$ is independently selected from the group consisting of H, $C_1$-$C_{10}$ alkyl, $C_1$-$C_{10}$ alkoxy, $C_3$-$C_{10}$ cycloalkyl, and $Ar_3$; and $Ar_1$, $Ar_2$, and $Ar_3$ are independently selected from the group consisting of

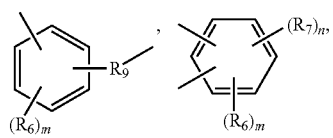

$R_6$ and $R_7$ are independently selected from the group consisting of H, $C_1$-$C_{10}$ alkyl group, $C_1$-$C_{10}$ alkoxy, and a cyclic alkyl group having 3-10 carbon atoms, M and n are independently an integer from 0 to 4;

$R_8$ is absent or is selected from the group consisting of —$CH_2$—, —$(CH_3)_2C$—, —$CO$—, —$SO_2$—, and —$O$—

$R_9$ is absent or is —$(CH_2)_p$, wherein p is an integer from 1 to 20;

A is selected from the group consisting of $C_1$-$C_{10}$ alkyl,

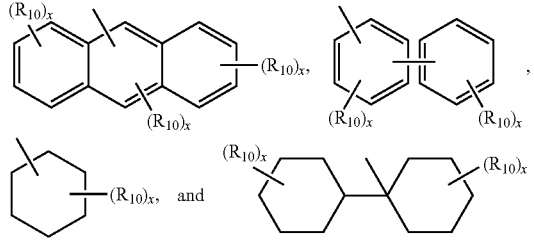

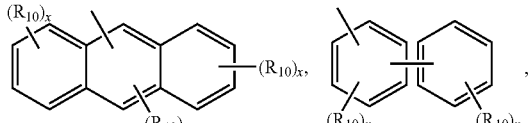

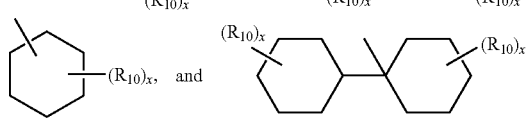

wherein, each $R_{10}$ is independently H or $C_1$-$C_{10}$ alkyl; and x is an integer from 0 to 4; and Ep is selected from the group consisting of:

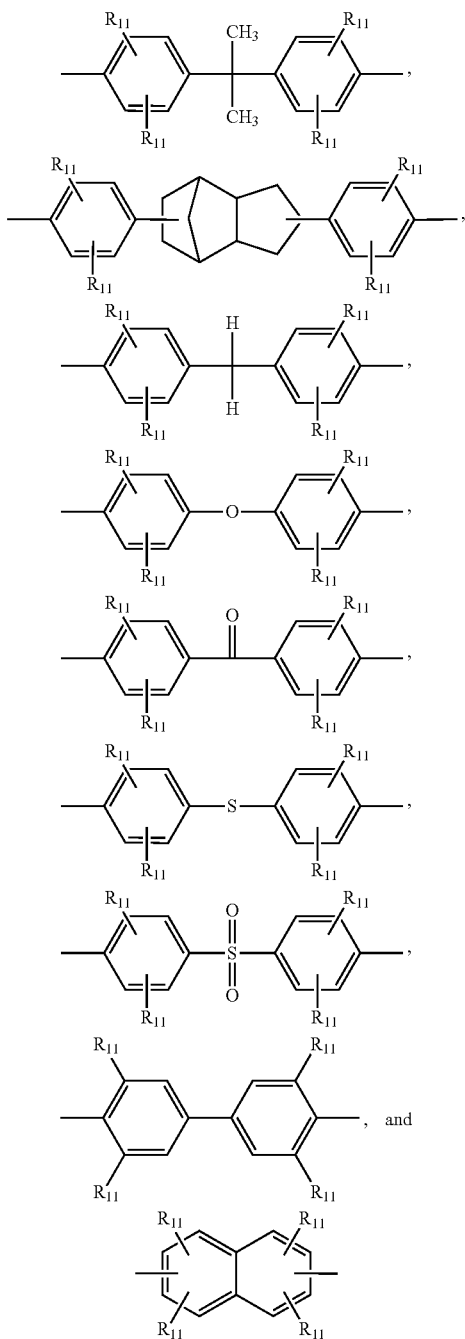

wherein each $R_{11}$ is independently selected from the group consisting of H, $C_1$-$C_6$ alkyl, $C_1$-$C_6$ alkoxy, a cyclic alkyl group having 3-7 carbon atoms, phenyl, and a phenoxyl group. In some cases, $R_{11}$ is independently H or a $C_1$-$C_{10}$ alkyl.

Finally, the instant disclosure relates to a method for synthesizing a compound described herein; to a flame retardant resinous compositions comprising the compounds described herein; and to a cured flame retardant resin prepared by cross-linking the flame retardant resinous composition.

DETAILED DESCRIPTION OF THE DISCLOSURE

The instant disclosure relates to compound of formula (I):

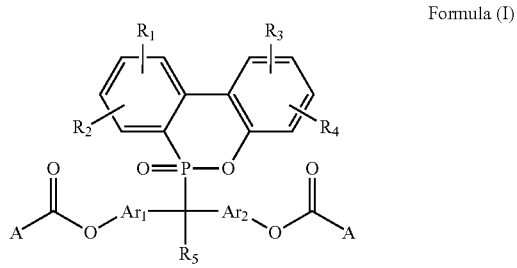

Formula (I)

wherein, $R_1$, $R_2$, $R_3$, and $R_4$ are independently selected from the group consisting of H, $C_1$-$C_{10}$, $C_1$-$C_{10}$ alkoxy, and $C_3$-$C_{10}$ cycloalkyl;

$R_5$ is independently selected from the group consisting of H, $C_1$-$C_{10}$ alkyl, $C_1$-$C_{10}$ alkoxy, $C_3$-$C_{10}$ cycloalkyl, and $Ar_3$; and $Ar_1$, $Ar_2$, and $Ar_3$ are independently selected from the group consisting of

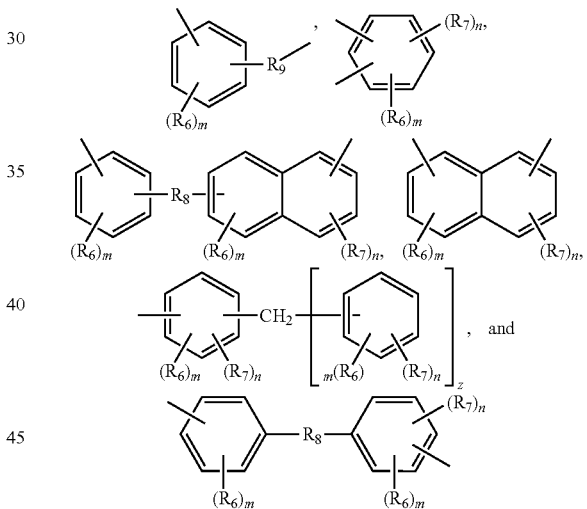

$R_6$ and $R_7$ are independently selected from the group consisting of H, $C_1$-$C_{10}$ alkyl group, $C_1$-$C_{10}$ alkoxy, and a cyclic alkyl group having 3-10 carbon atoms, M and n are independently an integer from 0 to 4;

$R_8$ is absent or is selected from the group consisting of —$CH_2$—, —$(CH_3)_2C$—), —CO—, —$SO_2$—, and —O—

$R_9$ is absent or is —$(CH_2)_p$—, wherein p is an integer from 1 to 20;

A is selected from the group consisting of $C_1$-$C_{10}$ alkyl,

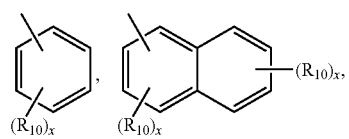

-continued

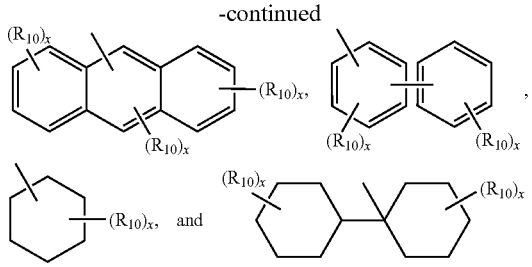

wherein, each $R_{10}$ is independently H or $C_1$-$C_{10}$ alkyl; and x is an integer from 0 to 4.

In some instances, $R_5$ is H or $C_1$-$C_{10}$ alkyl. In other instances, $Ar_1$ and $Ar_2$ are

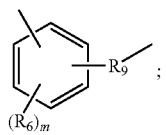

and in some instances $R_9$ may be absent.

In some instances, $R_1$, $R_2$, $R_3$, and $R_4$ are hydrogen. In other instances, A is $C_1$-$C_{10}$ alkyl,

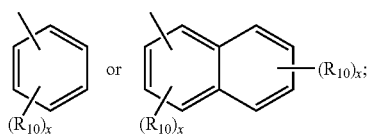

and in some instances, x is zero.

The instant disclosure also relates to a compound of formula (Ia)

Formula (Ia)

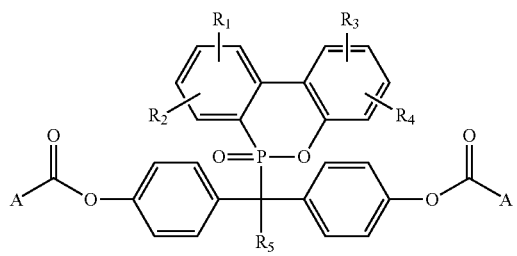

wherein, $R_1$, $R_2$, $R_3$, and $R_4$ are independently selected from the group consisting of H, $C_1$-$C_{10}$, $C_1$-$C_{10}$ alkoxy, and $C_3$-$C_{10}$ cycloalkyl;

$R_5$ is independently selected from the group consisting of H, $C_1$-$C_{10}$ alkyl, $C_1$-$C_{10}$ alkoxy, $C_3$-$C_{10}$ cycloalkyl, and $Ar_3$; and $Ar_3$ is independently selected from the group consisting of

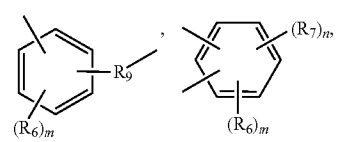

-continued

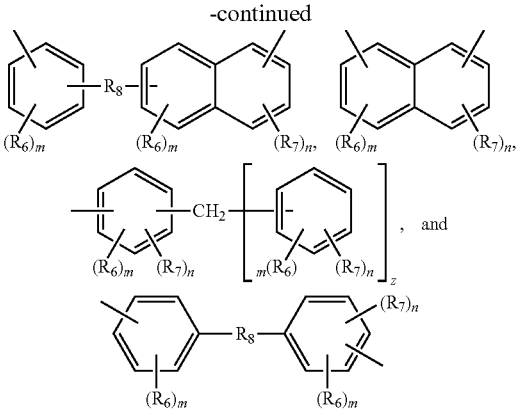

$R_6$ and $R_7$ are independently selected from the group consisting of H, $C_1$-$C_{10}$ alkyl group, $C_1$-$C_{10}$ alkoxy, and a cyclic alkyl group having 3-10 carbon atoms, M and n are independently an integer from 0 to 4;

$R_8$ is absent or is selected from the group consisting of —$CH_2$—, —$(CH_3)_2CH_2$—, —CO—, —$SO_2$—, and —O—

$R_9$ is absent or is —$(CH_2)_p$—, wherein p is an integer from 1 to 20; and

A is selected from the group consisting of $C_1$-$C_{10}$ alkyl,

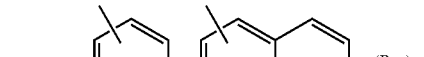

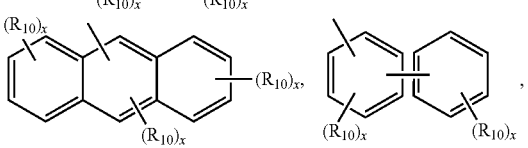

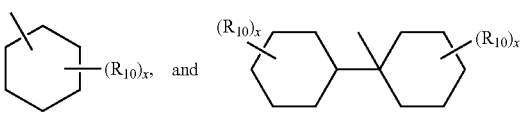

wherein, each $R_{10}$ is independently H or $C_1$-$C_{10}$ alkyl; and x is an integer from 0 to 4.

In some cases, $R_5$ is H or $C_1$-$C_{10}$ alkyl; and in some cases $R_5$ is methyl. In some cases, $R_1$, $R_2$, $R_3$, and $R_4$ are hydrogen. Furthermore, A can be a $C_1$-$C_{10}$ alkyl,

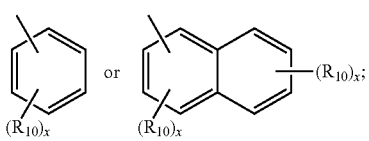

and in some cases x may be zero.

The instant disclosure further relates to a compound selected from the group consisting of:

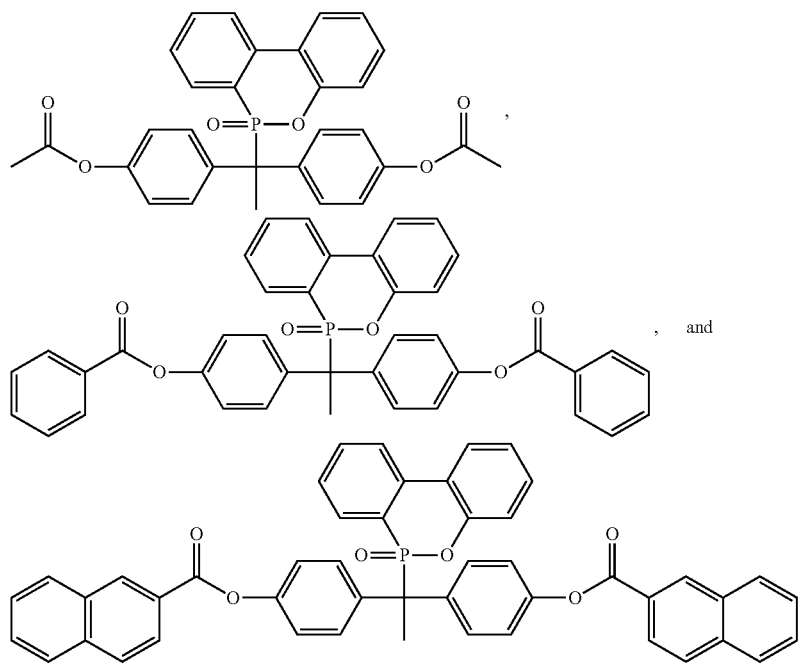

, and

The instant disclosure relates to a compound of Formula (II):

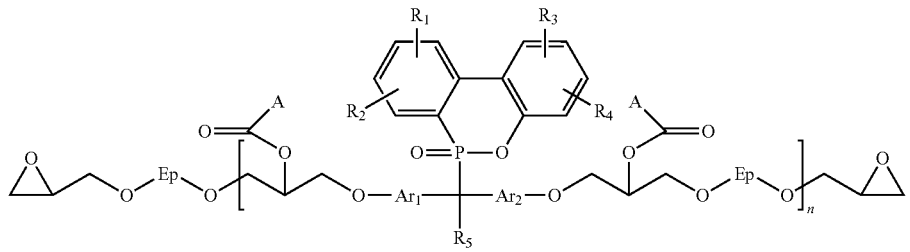

Formula (II)

wherein, $R_1$, $R_2$, $R_3$, and $R_4$ are independently selected from the group consisting of H, $C_1$-$C_{10}$, $C_1$-$C_{10}$ alkoxy, and $C_3$-$C_{10}$ cycloalkyl;

$R_5$ is independently selected from the group consisting of H, $C_1$-$C_{10}$ alkyl, $C_1$-$C_{10}$ alkoxy, $C_3$-$C_{10}$ cycloalkyl, and $Ar_3$; and $Ar_1$, $Ar_2$, and $Ar_3$ are independently selected from the group consisting of

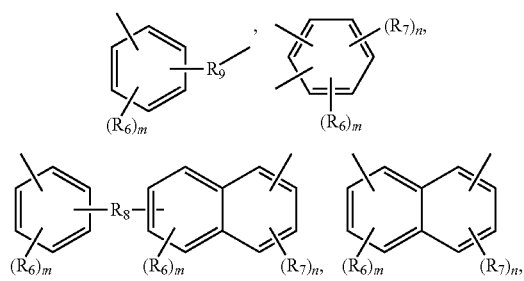

-continued

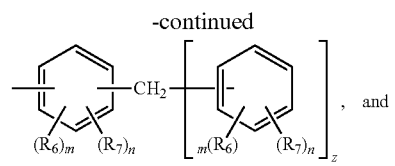

, and

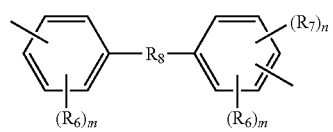

$R_6$ and $R_7$ are independently selected from the group consisting of H, $C_1$-$C_{10}$ alkyl group, $C_1$-$C_{10}$ alkoxy, and a cyclic alkyl group having 3-10 carbon atoms, M and n are independently an integer from 0 to 4;

$R_8$ is absent or is selected from the group consisting of —$CH_2$—, —$(CH_3)_2C$—, —CO—, —$SO_2$—, and —O—

$R_9$ is absent or is $-(CH_2)_p$, wherein p is an integer from 1 to 20;

A is selected from the group consisting of $C_1$-$C_{10}$ alkyl,

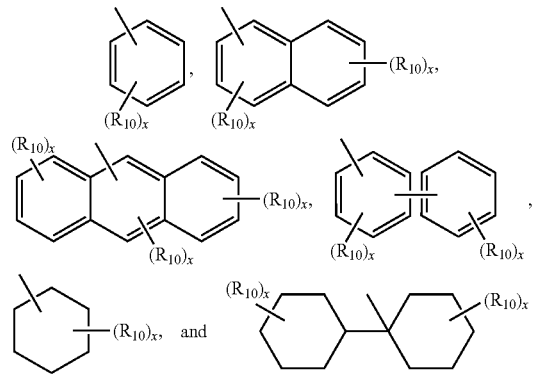

wherein, each $R_{10}$ is independently H or $C_1$-$C_{10}$ alkyl; and x is an integer from 0 to 4; and Ep is selected from the group consisting of:

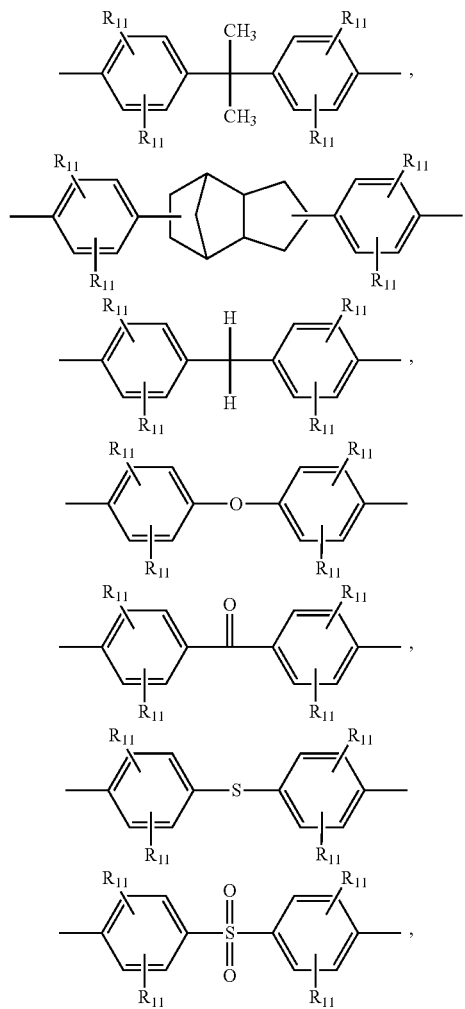

-continued

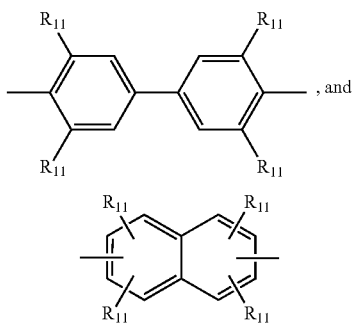

wherein each $R_{11}$ is independently selected from the group consisting of H, $C_1$-$C_6$ alkyl, $C_1$-$C_6$ alkoxy, a cyclic alkyl group having 3-7 carbon atoms, phenyl, and a phenoxyl group. In some cases, $R_{11}$ is independently H or a $C_1$-$C_{10}$ alkyl.

In the compound of Formula (II), Ep may be selected from the group consisting of:

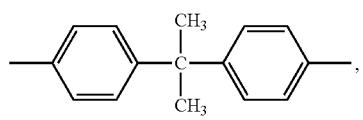

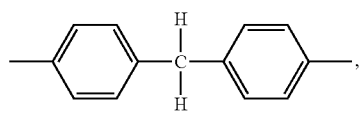

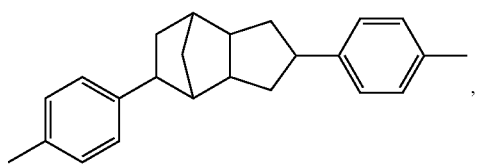

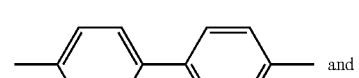

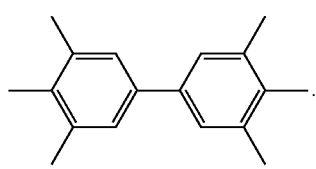

The instant disclosure further relates to a flame retardant resinous composition comprising a compound of formula (I) as defined above; and to a cured flame retardant resin prepared by cross-linking the flame retardant resinous composition.

Finally, the instant disclosure relates to a method for synthesizing a compound of Formula (II)

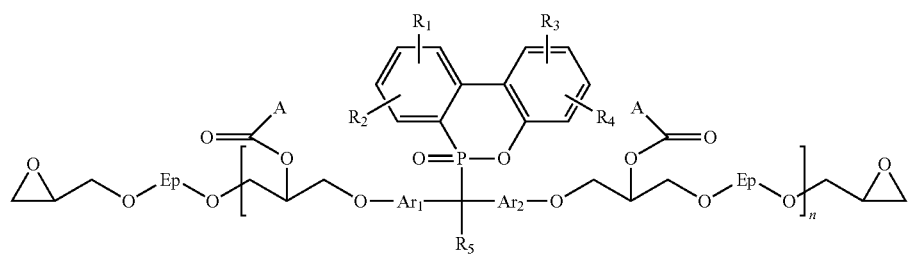

Formula (II)

comprising performing a catalytic reaction of a compound of formula (I)

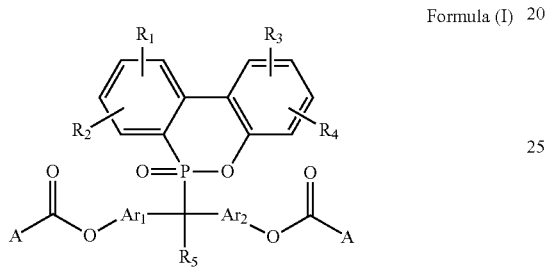

Formula (I)

with an epoxy monomer of formula (III)

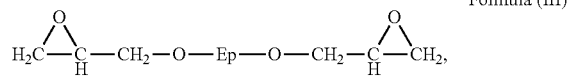

Formula (III)

wherein the substituents for Formula (I), (II), and (III), are defined above. In some instances, the reaction temperature is 100-200° C., 100-150° C., or 120-160° C. The equivalent ratio of the epoxy monomer of formula (III) to the compound of formula (I) is 1:1 to 10:1, 1:1 to 5:1, or 1:2 to 5:1. The amount of catalyst used to catalyze the reaction is 0.1-5 wt. %, 0.1-3 wt. %, or 0.2 to 0.5 wt. %, based on the amount of the epoxy monomer defined by the formula (III). In some cases, the catalyst is an imidazole, a tertiary amine, a tertiary phosphine, a quaternary ammonium salt, a quaternary phosphonium salt, a boron trifluoride complex, or a lithium compound. In particular, the catalyst may be an imidazole selected from the group consisting of 2-phenylimidazole and 2-methylimidazole; or the catalyst may be triphenylphosphine (a tertiary amine). In some cases, the catalyst is a quaternary ammonium salt selected from the group consisting of benzyltrimethyl ammonium chloride, benzyltriethyl ammonium chloride, and tetrabutyl ammonium chloride. Finally, the catalyst may be a quaternary phosphonium salt selected from the group consisting of ethyltriphenyl phosphonium acetate and a ethyltriphenyl phosphonium halide.

EXAMPLE 1

(Synthesis of Phosphorus Containing Bisphenol Compound A1) (DMP)

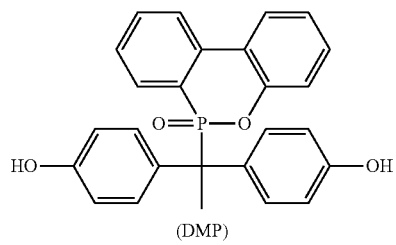

Compound A1

(DMP)

10.81 g (0.05 mole) of 9,10-dihydro-9-oxa-10-phosphaphenanthrene-10-oxide (DOPO), 23.5 g (0.25 mole) of phenol, 6.81 g (0.05 mole) of 4'-Hydroxyacetophenone, and 0.432 g (4 wt % based on the weight of DOPO) of p-toluenesulfonic acid were mixed and stirred in a 250 ml three-necked flask reactor at room temperature in advance. The reactants were stirred constantly at 130.degree. C. for 24 hours to form a mixture, and then the temperature of the mixture was cooled down to the room temperature. The crude products separated out from the cooled mixture were washed by ethanol and then filtrated and dried to obtain a white powder. The white powder was the phosphorus-containing bisphenol, and the chemical structure of the phosphorus-containing bisphenol A1.

The yield of the foregoing phosphorus-containing bisphenol was 85%, and the melting point was 306° C. The measured value of the carbon, hydrogen, and oxygen element were 72.48%, 4.65%, and 14.90%, respectively (the theoretical value, C, 72.89%; H, 4.65%; O, 14.94%.) by element analysis.

EXAMPLE 2

Synthesis of Phosphorus Containing Bisphenol Compound A2

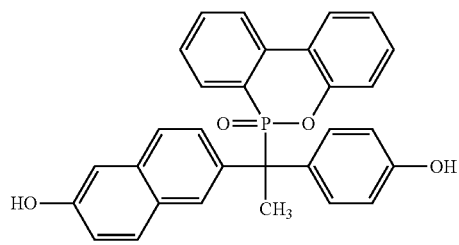

Compound A2

10.81 g (0.05 mole) of DOPO, 36 g (0.25 mole) of 2-naphthol, 6.81 g (0.05 mole) of 4'-Hydroxyacetophenone, and 0.432 g (4 wt % based on the Weight of DOPO) of p-toluene sulfonic acid were mixed and stirred in a 250 ml three-necked flask reactor at room temperature in advance. The reactants were stirred constantly at 130° C. for 24 hours to form a mixture, and then the temperature of the mixture was cooled down to the room temperature. The crude products separated out from the cooled mixture were washed by ethanol and then filtrated and dried to obtain a white powder. The white powder was the phosphorus-containing compound $A_2$.

The yield of the foregoing phosphorus-containing bisphenol was 85%, and the melting point was 317° C. The measured value of the carbon, hydrogen, and oxygen element were 75.54%, 4.58%, and 13.56%, respectively (the theoretical value, C, 75.31%; H, 4.85%; O, 13.38%.) by element analysis.

EXAMPLE 3

Synthesis of Phosphorus Containing Bisphenol A3

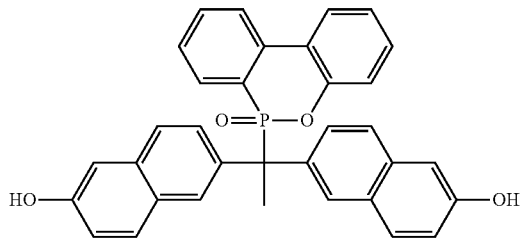

Compound A3

10.81 g (0.05 mole) of DOPO, 36 g (0.25 mole) of 2-naphthol, 9.01 g (0.05 mole) of 6-acetyl-2-naphthol, and 0.432 g (4 wt % based on the Weight of DOPO) of p-toluene sulfonic acid were mixed and stirred in a 250 ml three-necked flask reactor at room temperature in advance. The reactants were stirred constantly at 130° C. for 24 hours to form a mixture, and then the temperature of the mixture was cooled down to the room temperature. The crude products separated out from the cooled mixture were washed by ethanol and then filtrated and dried to obtain a white powder. The white powder was the phosphorus-containing compound A3.

The yield of the foregoing phosphorus-containing bisphenol was 80%, and the melting point was 338° C. The measured value of the carbon, hydrogen, and oxygen element were 77.69%, 4.17%, and 12.25%, respectively (the theoretical value, C, 77.26%; H, 4.76%; O, 12.11%.) by element analysis.

EXAMPLE 4

Synthesis of Ester Substituted Phosphorous-Containing Bisphenol Compound B1

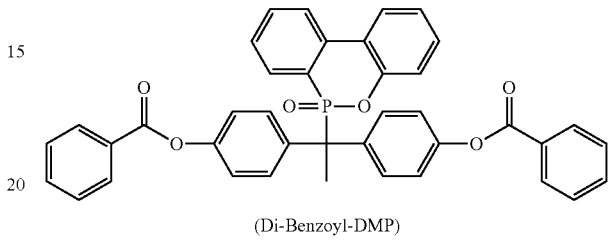

Compound B1

(Di-Benzoyl-DMP)

DMP (Phosphorous containing bisphenol Compound A1) 428 g (1 mol), Potassium carbonate ($K_2CO_3$) 303.9 g (2.2 mol) and acetone 1000 g were placed into a in a five-neck glass reaction kettle equipped with an electric heating jacket, a temperature controller, an electric stirrer and a stirring bar, a nitrogen gas inlet, a thermocouple, a water-cooled condenser, and a feeding funnel. At first, benzoyl chloride 309.5 g (2.2 mol) was dropped into the reactor at 50° C. within 1 hour, then reacted 4 hours. Afterwards, substances were cooled to the room temperature. In the same time, the ester substituted phosphorous bisphenol compound and by-product salt which is generated by the addition reaction precipitated in the reactor. In order to eliminate the reaction byproduct salt, using water to wash the precipitant then isolated the product by filtration. Finally, Dried the product at a temperature of 120° C. The white powder is ester substituted of Phosphorous bisphenol compound B1, FT-IR analysis indicated that the 3300 cm-1 peak of OH group was not detected and the 1700 cm-1 peak of carbonyl group was detected. The yield of the foregoing ester substituted phosphorus-containing bisphenol was 88%, melting point: 180° C.

EXAMPLE 5

(Synthesis of Ester Substituted Phosphorous Containing Bisphenol Compound B2)
(Dinaphthoyl-DMP)

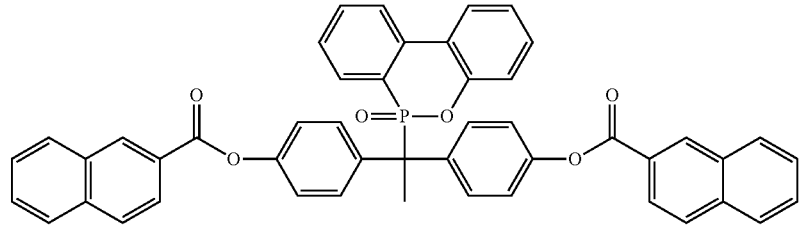

Compound B2)

(Dinaphthoyl-DMP)

DMP (phosphorous containing bisphenol compound A1) 428 g (1 mol), potassium carbonate (K2CO3) 303.9 g (2.2 mol) and acetone 1000 g were placed into a in a five-neck glass reaction kettle equipped with an electric heating jacket, a temperature controller, an electric stirrer and a stirring bar, a nitrogen gas inlet, a thermocouple, a water-cooled condenser, and a feeding funnel. At first, naphthoyl chloride 418 g (2.2 mol) was dropped into the reactor at 50° C. within 1 hour, then reacted 4 hours. Afterwards, substances were cooled to the room temperature. In the same time, the ester substituted phosphorous bisphenol compound and by-product salt which is generated by the addition reaction precipitated in the reactor. In order to eliminate the reaction byproduct salt, using water to wash the precipitant then isolated the product by filtration. Finally, dried the product at a temperature of 120° C. The white powder is ester substituted of phosphorous bisphenol compound B2, FT-IR analysis indicated that the 3300 cm-1 peak of OH group was not detected and the 1700 cm-1 peak of carbonyl group was detected, The yield of the foregoing ester substituted phosphorus-containing bisphenol was 85%. Melting point: 180° C.

EXAMPLE 6

(Synthesis of Ester Substituted Phosphorous Containing Bisphenol Compound B3) (Diacetyl-DMP)

Compound B3

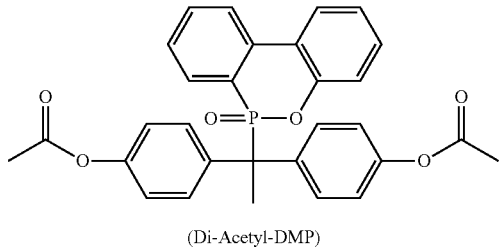

(Di-Acetyl-DMP)

DMP (phosphorous containing bisphenol compound A1) 428 g (1 mol), potassium carbonate (K2CO3) 303.9 g (2.2 mol) and acetone 1000 g were placed into a in a five-neck glass reaction kettle equipped with an electric heating jacket, a temperature controller, an electric stirrer and a stirring bar, a nitrogen gas inlet, a thermocouple, a water-cooled condenser, and a feeding funnel. At first, acetyl chloride 172.7 g (2.2 mol) was dropped into the reactor at 50° C. within 1 hour, then reacted 4 hours. Afterwards, substances were cooled to the room temperature. In the same time, the ester substituted phosphorous bisphenol compound and by-product salt which is generated by the addition reaction were precipitated in the reactor. In order to eliminate the reaction byproduct salt, using water to wash the precipitant then isolated the product by filtration. Finally, dried the product at a temperature of 120° C. The white powder is ester substituted of Phosphorous bisphenol compound B3

FT-IR analysis indicated that the 3300 cm-1 peak of OH group was not detected and the 1700 cm-1 peak of carbonyl group was detected, The yield of the foregoing ester substituted phosphorus-containing bisphenol was 89%. Melting point: 180° C.

EXAMPLE 7

Synthesis of Ester Substituted Phosphorous Containing Bisphenol Compound B4

Compound B4

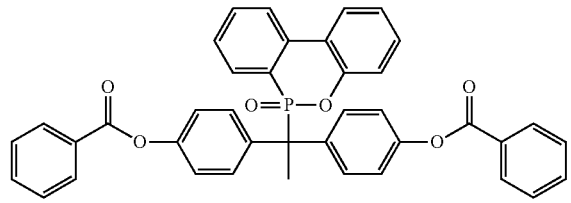

DMP (phosphorous containing bisphenol compound A1) 428 g (1 mol), Benzoic acid anhydride 497.7 g (2.2 mol) and 1-methyl imidazole 0.173 g were placed into a in a five-neck glass reaction kettle equipped with an electric heating jacket, a temperature controller, an electric stirrer and a stirring bar, a nitrogen gas inlet, a thermocouple, a water-cooled condenser, and a feeding funnel. At first, benzoyl anhydride 497.7 g (2.2 mol) was dropped into the reactor at 50° C. within 1 hour, then reacted 4 hours. Afterwards, substances were cooled to the room temperature. In the same time, the ester substituted phosphorous bisphenol compound and by-product salt which is generated by the addition reaction precipitated in the reactor. In order to eliminate the reaction byproduct salt, using water to wash the precipitant then isolated the product after filtration. Finally, dried the product at a temperature of 120° C. The white powder is ester substituted of phosphorous bisphenol compound B4.

FT-IR analysis indicated that the 3300 cm-1 peak of OH group was not detected and the 1700 cm-1 peak of carbonyl group was detected, The yield of the foregoing ester substituted phosphorus-containing bisphenol was 79%. Melting point: 180° C.

EXAMPLE 8

Synthesis of Ester Substituted Phosphorous Containing Bisphenol Compound B5

Compound B5

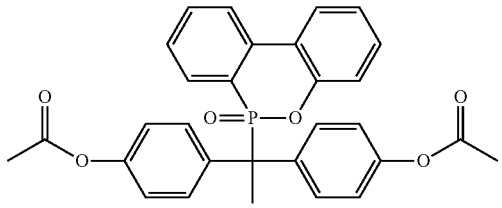

DMP (phosphorous containing bisphenol compound A1) 428 g (1 mol), acetic acid anhydride 340 g (2.2 mol) and 1-methyl imidazole 0.173 g were placed into a in a five-neck glass reaction kettle equipped with an electric heating jacket, a temperature controller, an electric stirrer and a stirring bar, a nitrogen gas inlet, a thermocouple, a water-cooled condenser, and a feeding funnel. At first, acetic anhydride 340 g (2.2 mol) was dropped into the reactor at 50° C. within 1 hour, then reacted 4 hours. Afterwards, substances were cooled to the room temperature. In the same time, the ester substituted phosphorous bisphenol compound and by-product salt which is generated by the addition reaction precipitated in the reactor. In order to eliminate the reaction byproduct salt, using water to wash the precipitant then isolated the product after filtration. Finally, Dried the product at a temperature of 120° C. The white powder is ester substituted of Phosphorous bisphenol compound B5

FT-IR analysis indicated that the 3300 cm-1 peak of OH group was not detected and the 1700 cm-1 peak of carbonyl group was detected, The yield of the foregoing ester substituted phosphorus-containing bisphenol was 81%. Melting point: 180° C.

Examples 9-31

The following components are used in Examples 9-26:

| | |
|---|---|
| Epoxy resin 1 | A diglycidyl ether of bisphenol A having an epoxy equivalent Weight of 175-185 grams/equivalent, a hydrolyzable chloride of below 200 ppm, a viscosity of 7000-10000 cp, under trade name of BE186LG sold and manufactured by Chang Chun Plastic Co., Ltd., Taiwan, R.O.C. 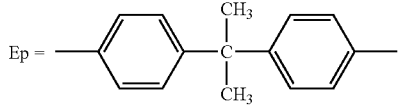 |
| Epoxy resin 2 | A diglycidyl ether of bisphenol F having an epoxy equivalent Weight of 163-173 grams/equivalent, a hydrolyzable chloride of below 200 ppm, a viscosity of 2500-4500 cp, under trade name of BFE170 sold and manufactured by Chang Chun Plastic Co., Ltd., Taiwan, R.O.C. 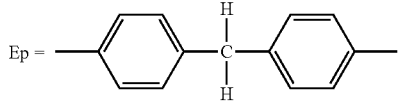 |
| Epoxy resin 3 | A diglycidyl ether of 3,3',5,5'-tetramethyl-4,4'-biphenol having an epoxy equivalent Weight of 180 to 200 grams/equivalent, under trade name of YX4000H sold and manufactured by Yuka Shell Epoxy Co. Ltd., Japan. |
| Epoxy resin 4 | A polyglycidyl ether of dicyclodipentadiene having an epoxy equivalent weight of 240-270 grams/equivalent, under trade name of DNE260 sold and manufactured by Chang Chun Plastic Co., Ltd., Taiwan, R.O.C. 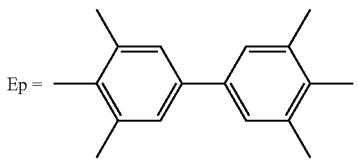 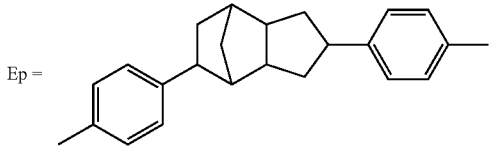 |
| Epoxy resin 5 | A phosphorus containing polyglycidyl ether of phenolic condensate having an epoxy equivalent weight of 260-300 grams/equivalent, a solid content of 75% under trade name of BEP280A75 sold and manufactured by Chang Chun Plastic Co., Ltd., Taiwan, R.O.C. 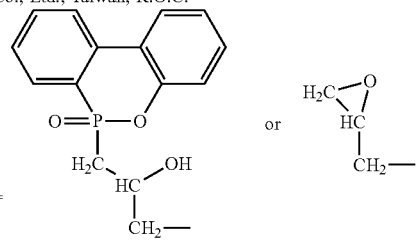 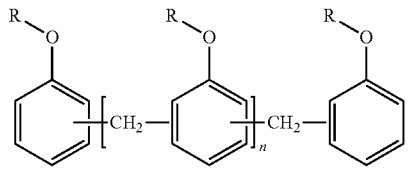 |
| Curing agent A | Dicyandiamide (DICY), 10% dissolved in dimethylformamide. |
| Curing agent B | Nitrogen containing phenolic resin dissolved in cyclohexanol. The solid content is 60% |
| Catalyst A | triphenylphosphine. (TPP), 10% dissolved in methylethylketone |
| Catalyst B | 2-methylimidazole (hereinafter referred to 2MI)., 10% dissolved in methanol |

EXAMPLE 9

Synthesis of Phosphorous Containing Epoxy C1

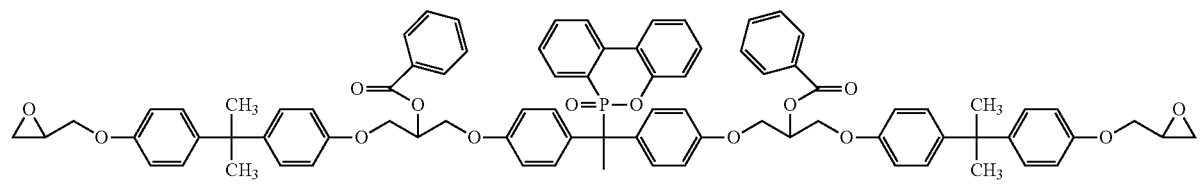

Epoxy C1

Epoxy resin 1 (100 g) and ester substituted phosphorus compound B1 (Dibenzyl-DMP) (70 g) were placed in a five-neck glass reaction kettle equipped with an electric heating jacket, a temperature controller, an electric stirrer and a stirring bar, a nitrogen gas inlet, a thermocouple, a water-cooled condenser, and a feeding funnel. Nitrogen gas was introduced and the reaction kettle was heated to 130° C. After epoxy resin A and ester substituted phosphorus compound B1 completely melted, the raw materials were dried under vacuum. The steps of introducing nitrogen gas and drying were carried out two more times. When the temperature of the reaction kettle was decreased from 100° C., catalyst A (0.8 g) was added. The stirrer was started to mix the resin and catalyst and the nitrogen gas was introduced. The resulting mixture was heated to 170° C. It was found that the reactants were slowly exothermic. The reactants were maintained at 170° C. for 2.5 hours and the phosphorus-containing epoxy (Epoxy C1) was obtained. The equivalent weight was 507.2, and the theoretical phosphorus content was 2.0 wt %. For uniformity, the product was dissolved in the methyl ethyl ketone (MEK) and the solid content adjusted to 70%.

EXAMPLE 10

Synthesis of Phosphorous Containing Epoxy C2

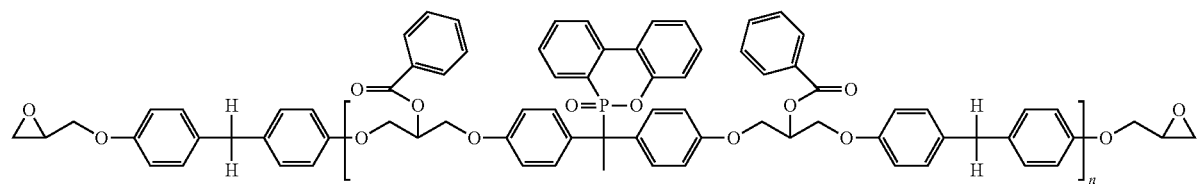

Epoxy C2

Epoxy resin 2 (100 g) and ester substituted phosphorus compound B1 (Dibenzyl-DMT) (70 g) were placed in a five-neck glass reaction kettle equipped with an electric heating jacket, a temperature controller, an electric stirrer and a stirring bar, a nitrogen gas inlet, a thermocouple, a water-cooled condenser, and a feeding funnel. Nitrogen gas was introduced and the reaction kettle was heated to 130° C. After epoxy resin 2 and ester substituted phosphorus compound B1 completely melted, the raw materials were dried under vacuum. The steps of introducing nitrogen gas and drying were carried out two more times. When the temperature of the reaction kettle was decreased from 100° C., catalyst A (0.8 g) was added. The stirrer was started to mix the resin and catalyst and the nitrogen gas was introduced. The resulting mixture was heated to 170° C. It was found that the reactants were slowly exothermic. The reactants were maintained at 170° C. for 2.5 hours and the phosphorus-containing epoxy (Epoxy C2) was obtained. The epoxy equivalent weight was 455.3, and the theoretical phosphorus content was 2.0 wt %. For uniformity, the product was dissolved in the methyl ethyl ketone (MEK) and the solid content adjusted to 70%.

EXAMPLE 11

Synthesis of Phosphorous Containing Epoxy C3

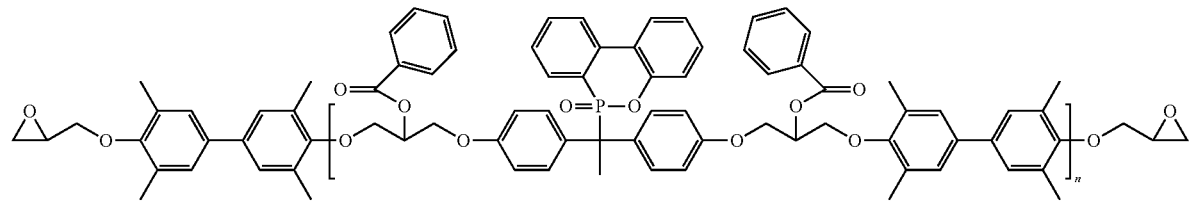

Epoxy C3

Epoxy resin 3 (100 g) and ester substituted phosphorus compound B1 (Dibenzyl-DMP) (70 g) were placed in a five-neck glass reaction kettle equipped with an electric heating jacket, a temperature controller, an electric stirrer and a stirring bar, a nitrogen gas inlet, a thermocouple, a water-cooled condenser, and a feeding funnel. Nitrogen gas was introduced and the reaction kettle was heated to 130° C. After epoxy resin 3 and ester substituted phosphorus compound B1 completely melted, the raw materials were dried under vacuum. The steps of introducing nitrogen gas and drying were carried out two more times. When the temperature of the reaction kettle was decreased from 100° C., catalyst A (0.8 g) was added. The stirrer was started to mix the resin and catalyst and the nitrogen gas was introduced. The resulting mixture was heated to 170° C. It was found that the reactants were slowly exothermic. The reactants were maintained at 170° C. for 2.5 hours and the phosphorus-containing epoxy (Epoxy C3) was obtained. The epoxy equivalent weight was 545.2, and the theoretical phosphorus content was 2.0 wt %. For uniformity, the product was dissolved in the methyl ethyl ketone (MEK) and the solid content adjusted to 70%.

EXAMPLE 12

Synthesis of Phosphorous Containing Epoxy C4

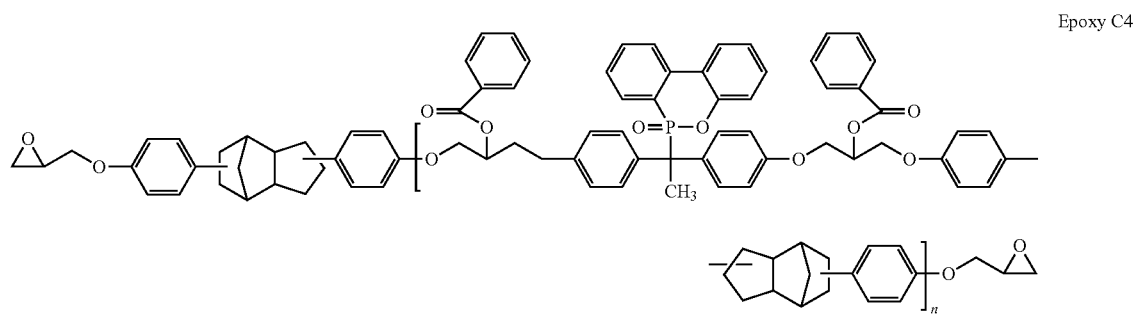
Epoxy C4

Epoxy resin 4 (100 g) and ester substituted phosphorus compound B1 (Dibenzyl-DMP) (70 g) were placed in a five-neck glass reaction kettle equipped with an electric heating jacket, a temperature controller, an electric stirrer and a stirring bar, a nitrogen gas inlet, a thermocouple, a water-cooled condenser, and a feeding funnel. Nitrogen gas was introduced and the reaction kettle was heated to 130° C. After epoxy resin 4 and ester substituted phosphorus compound B1 completely melted, the raw materials were dried under vacuum. The steps of introducing nitrogen gas and drying were carried out two more times. When the temperature of the reaction kettle was decreased from 100° C., catalyst A (0.8 g) was added. The stirrer was started to mix the resin and catalyst and the nitrogen gas were introduced. The resulting mixture was heated to 170° C. It was found that the reactants were slowly exothermic. The reactants were maintained at 170° C. for 2.5 hours and the phosphorus-containing epoxy (Epoxy C4) was obtained. The epoxy equivalent weight was 870, and the theoretical phosphorus content was 2.0 wt %. For uniformity, the product was dissolved in the methyl ethyl ketone (MEK) and the solid content adjusted to 70%.

EXAMPLE 13

Synthesis of Phosphorous Containing Epoxy C5

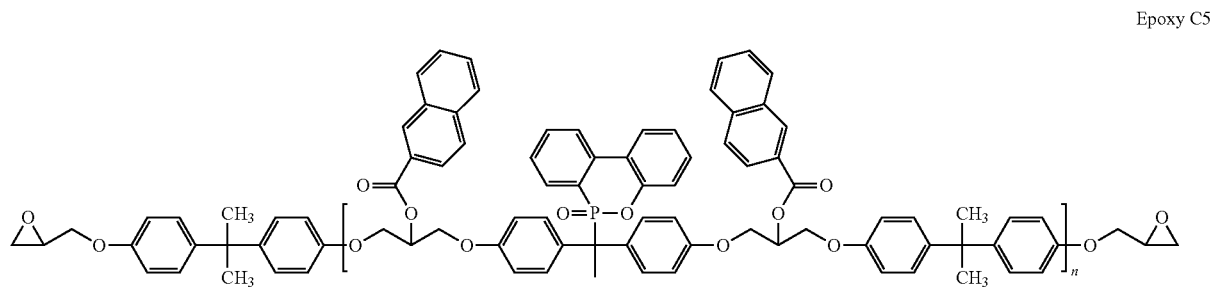
Epoxy C5

Epoxy resin 1 (100 g) and ester substituted phosphorus compound B2 (Dinaphthoyl-DMP) (91 g) were placed in a five-neck glass reaction kettle equipped with an electric heating jacket, a temperature controller, an electric stirrer and a stirring bar, a nitrogen gas inlet, a thermocouple, a water-cooled condenser, and a feeding funnel. Nitrogen gas was introduced and the reaction kettle was heated to 130° C. After epoxy resin 1 and ester substituted phosphorus compound B2 completely melted, the raw materials were dried under vacuum. The steps of introducing nitrogen gas and drying were carried out two more times. When the temperature of the reaction kettle was decreased from 100° C., catalyst A (0.9 g) was added. The stirrer was started to mix the resin and catalyst and the nitrogen gas were introduced. The resulting mixture was heated to 170° C. It was found that the reactants were slowly exothermic. The reactants were maintained at 170° C. for 2.5 hours and the phosphorus-containing epoxy (Epoxy C5) was obtained. The epoxy equivalent weight was 617.8, and the theoretical phosphorus content was 2.0 wt %. For uniformity, the product was dissolved in the methyl ethyl ketone (MEK) and the solid content adjusted to 70%.

EXAMPLE 14

Synthesis of Phosphorous Containing Epoxy C6

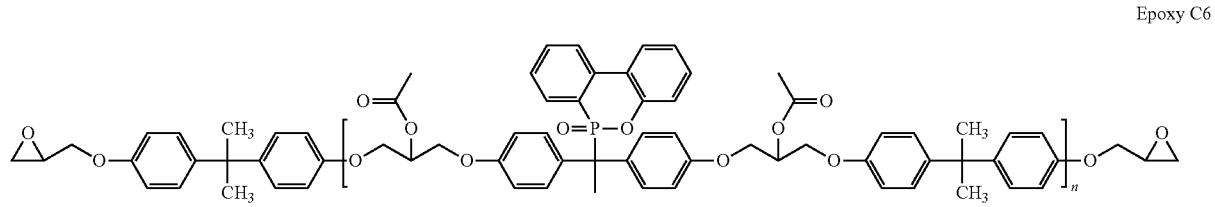

Epoxy C6

Epoxy resin 1 (100 g) and ester substituted phosphorus compound B3 (Diacetyl-DMP) 50 g) were placed in a five-neck glass reaction kettle equipped with an electric heating jacket, a temperature controller, an electric stirrer and a stirring bar, a nitrogen gas inlet, a thermocouple, a water-cooled condenser, and a feeding funnel. Nitrogen gas was introduced and the reaction kettle was heated to 130° C. After epoxy resin 1 and ester substituted phosphorus compound B3 completely melted, the raw materials were dried under vacuum. The steps of introducing nitrogen gas and drying were carried out two more times. When the temperature of the reaction kettle was decreased from 100° C., catalyst A (0.8 g) was added. The stirrer was started to mix the resin and catalyst and the nitrogen gas was introduced. The resulting mixture was heated to 170° C. It was found that the reactants were slowly exothermic. The reactants were maintained at 170° C. for 2.5 hours and the phosphorus-containing epoxy (Epoxy C6) was obtained. The epoxy equivalent weight was 414.8, and the theoretical phosphorus content was 2.0 wt %. For uniformity, the product was dissolved in the methyl ethyl ketone (MEK) and the solid content adjusted to 70%.

EXAMPLE 15

Synthesis of Phosphorous Containing Epoxy C7

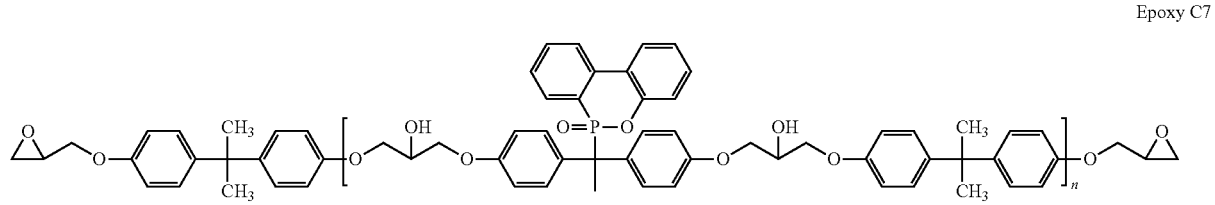

Epoxy C7

Epoxy resin 1 (100 g) and ester substituted phosphorus compound A1 (DMP) (39 g) were placed in a five-neck glass reaction kettle equipped with an electric heating jacket, a temperature controller, an electric stirrer and a stirring bar, a nitrogen gas inlet, a thermocouple, a water-cooled condenser, and a feeding funnel. Nitrogen gas was introduced and the reaction kettle was heated to 130° C. After epoxy resin 1 and ester substituted phosphorus compound A1 completely melted, the raw materials were dried under vacuum. The steps of introducing nitrogen gas and drying were carried out two more times. When the temperature of the reaction kettle was decreased from 100° C., catalyst A Epoxy C9

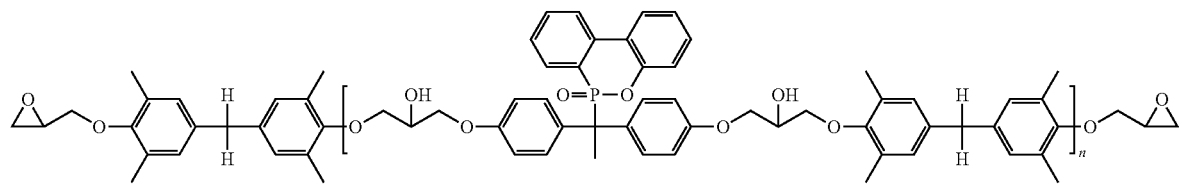

(0.7 g) was added. The stirrer was started to mix the resin and catalyst and the nitrogen gas was introduced. The resulting mixture was heated to 170° C. It was found that the reactants were slowly exothermic. The reactants were maintained at 170° C. for 2.5 hours and the phosphorus-containing epoxy (Epoxy C7) was obtained. The epoxy equivalent weight was 370.9, and the theoretical phosphorus content was 2.0 wt %. For uniformity, the product was dissolved in the methyl ethyl ketone (MEK) and the solid content adjusted to 70%.

EXAMPLE 16

Synthesis of Phosphorous Containing Epoxy C8 tained at 170° C. for 2.5 hours and the phosphorus-containing epoxy (Epoxy C8) was obtained. The epoxy equivalent weight was 336.6, and the theoretical phosphorus content was 2.0 wt %. For uniformity, the product was dissolved in the methyl ethyl ketone (MEK) and the solid content adjusted to 70%.

EXAMPLE 17

Synthesis of Phosphorous Containing Epoxy C9

Epoxy resin 3 (100 g) and ester substituted phosphorus compound A1 (DMP) (39 g) were placed in a five-neck glass reaction kettle equipped with an electric heating jacket, a temperature controller, an electric stirrer and a stirring bar, a nitrogen gas inlet, a thermocouple, a water-cooled condenser, and a feeding funnel. Nitrogen gas was introduced and the reaction kettle was heated to 130° C. After epoxy resin 3 and ester substituted phosphorus compound A1 completely melted, the raw materials were dried under vacuum. The steps of introducing nitrogen gas and drying were carried out two more times. When the temperature of the reaction kettle was decreased from 100° C., catalyst A (0.7 g) was added. The stirrer was started to mix the resin and catalyst and the nitrogen gas was introduced. The resulting mixture was heated to Epoxy C8

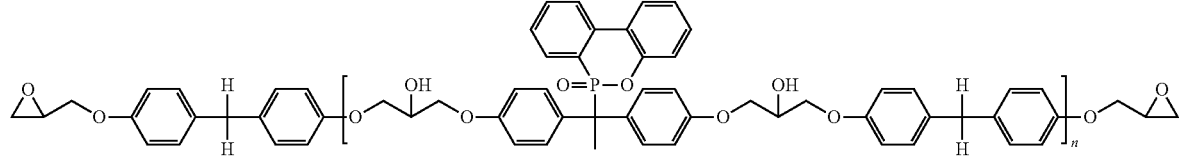

Epoxy resin 2 (100 g) and ester substituted phosphorus compound A1 (DMP) (39 g) were placed in a five-neck glass reaction kettle equipped with an electric heating jacket, a temperature controller, an electric stirrer and a stirring bar, a nitrogen gas inlet, a thermocouple, a water-cooled condenser, and a feeding funnel. Nitrogen gas was introduced and the reaction kettle was heated to 130° C. After epoxy resin 2 and ester substituted phosphorus compound A1 completely melted, the raw materials were dried under vacuum. The steps of introducing nitrogen gas and drying were carried out two more times. When the temperature of the reaction kettle was decreased from 100° C., catalyst A (0.7 g) was added. The stirrer was started to mix the resin and catalyst and the nitrogen gas was introduced. The resulting mixture was heated to 170° C. It was found that the reactants were slowly exothermic. The reactants were main- 17° C. It was found that the reactants were slowly exothermic. The reactants were maintained at 170° C. for 2.5 hours and the phosphorus-containing epoxy (Epoxy C9) was obtained. The epoxy equivalent weight was 395.6, and the theoretical phosphorus content was 2.0 wt %. For uniformity, the product was dissolved in the methyl ethyl ketone (MEK) and the solid content adjusted to 70%.

The compositions of Examples 9-17 were evaluated for epoxy equivalent weight (EEW) and solids content according to the following methods:

Epoxy equivalent weight (EEW): the epoxy resin can be determined according to the method in ASTM D1652.

Solid content: 1 gram of sample containing the phosphorus-containing epoxy resin was placed in an oven at 150° C.

for 60 minutes after which and the weight percentage of the resulting non-volatile components was measured.

The results are reported in Table 1 below.

TABLE 1

| | Examples 9-17 | | | | | | | | |
|---|---|---|---|---|---|---|---|---|---|
| Example No. | 9 | 10 | 11 | 12 | 13 | 14 | 15 | 16 | 17 |
| Phosphorous-Containing | $C_1$ | $C_2$ | $C_3$ | $C_4$ | $C_5$ | $C_6$ | $C_7$ | $C_8$ | $C_9$ |
| Epoxy Resin | | | | | | | | | |
| Epoxy resin 1 | 100 | | | | 100 | 100 | 100 | | |
| Epoxy resin 2 | | 100 | | | | | | 100 | |
| Epoxy resin 3 | | | 100 | | | | | | 100 |
| Epoxy resin 4 | | | | 100 | | | | | |
| Synthesis example 4 | 70 | 70 | 70 | 70 | | | | | |
| Synthesis example 5 | | | | | 91 | | | | |
| Synthesis example 6 | | | | | | 50 | | | |
| Synthesis example 1 | | | | | | | 39 | 39 | 39 |
| Catalyst A | 0.8 | 0.8 | 0.8 | 0.8 | 0.9 | 0.8 | 0.7 | 0.7 | 0.7 |
| Methyl Ethyl Ketone | 73 | 73 | 73 | 73 | 82.2 | 64 | 60 | 60 | 60 |
| EEW | 507.2 | 455.3 | 545.2 | 870 | 617.8 | 414.8 | 370.9 | 336.6 | 395.6 |
| Phosphorous content | 2.0% | 2.0% | 2.0% | 2.0 | 2.0% | 2.0% | 2.0% | 2.0% | 2.0% |
| Solid content | 70% | 70% | 70% | 70% | 70% | 70% | 70% | 70% | 70% |

EXAMPLES 18-31

Glass fiber fabric was impregnated with the phosphorus-containing epoxy resins of Examples 9-17 (Phosphorous-Containing Epoxy Resins $C_1$-$C_9$) and dried at 160° C. to form prepegs. Five pieces of the prepregs were piled up and a sheet of 35 μm copper foil was placed on the top and bottom and laminated at 210° C. under a pressure of 25 kg/cm$^2$. This resulted in a laminated entity of the phosphorus-containing epoxy resin and glass fiber fabric. The physical properties of each laminated entity were analyzed according to the following procedures.

Dielectric Constant (Dk) and Dissipation Factor (Df) were measured according to IPC-TM-650-2.5.5.9.

Peel Strength (1 oz copper) was measured according to IPC-TM-650-2.4.8.

Glass Transition Temperature (Tg) was measured according to IPC-TM-650-2.4.25 by using Differential Scanning Calorimetry (DSC) (Scan Rate: 20° C./min).

Coefficient Thermal Expansion (CTE, ppm/K) was measured according to IPC-TM-650-2.4.24 by TMA (thermo mechanical analysis) (α1 is the CTE value before Tg, α2 is the CTE value after Tg).

Decomposition Temperature (Td, 5% weight loss) was measured according to IPC-TM-650-2.3.40 using a thermogravimetric analyzer (TGA) (Scan Rate: 10° C./min).

Water Absorption (Wt %): To calculate the water absorption, the specimens were placed in a 100° C. water and the rof increase in weight (wt %) measured after two hours.

Thermal Stability (S-288) are measured according to JIS-C-6481: The laminated entity was immersed into a 288° C. solder furnace and the time to delamination measured.

Flame Retardancy was measured according to UL94.

| UL 94 Flammability Ratings Summary | |
|---|---|
| 5VA Surface Burn | Burning stops within 60 seconds after five applications of five seconds each of a flame (larger than that used in Vertical Burn testing) to a test bar. Test specimens MAY NOT have a burn-through (no hole). This is the highest (most flame retardant) UL94 rating. |
| 5VB Surface Burn | Burning stops within 60 seconds after five applications of five seconds each of a flame (larger than that used in Vertical Burn testing) to a test bar. Test specimens MAY HAVE a burn-through (a hole). |
| V-0 Vertical Burn | Burning stops within 10 seconds after two applications of ten seconds each of a flame to a test bar. NO flaming drips are allowed. |
| V-1 Vertical Burn | Burning stops within 60 seconds after two applications of ten seconds each of a flame to a test bar. NO flaming drips are allowed. |
| V-2 Vertical Burn | Burning stops within 60 seconds after two applications of ten seconds each of a flame to a test bar. Flaming drips ARE allowed |
| HB Horizontal Burn | Slow horizontal burning on a 3 mm thick specimen with a burning rate is less than 3"/min or stops burning before the 5" mark. H-B rated materials are considered "self-extinguishing". This is the lowest (least flame retardant) UL94 rating. |

The composition of Examples 18-31 are shown in Tables 2 and 2(a), and the measurements are reported in Tables 3 and 3(a).

TABLE 2

| | Examples 18-26 (Inventive) | | | | | | | | |
|---|---|---|---|---|---|---|---|---|---|
| Examples No. | 18 | 19 | 20 | 21 | 22 | 23 | 24 | 25 | 26 |
| Phosphorous epoxy $C_1$ (From Example 9) | 100 | | | | | | 100 | | |
| Phosphorous epoxy $C_2$ (From Example 10) | | 100 | | | | | | | |
| Phosphorous epoxy $C_3$ (From Example 11) | | | 100 | | | | | | |

TABLE 2-continued

| | Examples 18-26 (Inventive) | | | | | | | | |
|---|---|---|---|---|---|---|---|---|---|
| Examples No. | 18 | 19 | 20 | 21 | 22 | 23 | 24 | 25 | 26 |
| Phosphorous epoxy $C_4$ (From Example 12) | | | | 100 | | | | | |
| Phosphorous epoxy $C_5$ (From Example 13) | | | | | 100 | | | 100 | |
| Phosphorous epoxy $C_6$ (From Example 14) | | | | | | 100 | | | 100 |
| Curing agent A | 16.3 | 18.1 | 15.1 | 9.5 | 13.4 | 20.2 | | | |
| Curing agent B | | | | | | | 51.7 | 41.8 | 63.2 |
| Catalyst B | 0.5 | 0.5 | 0.5 | 0.5 | 0.5 | 0.5 | 0.5 | 0.5 | 0.5 |
| Acetone | 5 | 5 | 5 | 10 | 7 | 0 | 25 | 22 | 23 |

TABLE 2a

| | Examples 27-31 (Comparative) | | | | |
|---|---|---|---|---|---|
| | Examples No. | | | | |
| | 27 | 28 | 29 | 30 | 31 |
| Phosphorous epoxy $C_7$ (From Example 15) | 100 | | | 100 | |
| Phosphorous epoxy $C_8$ (From Example 16) | | 100 | | | |
| Phosphorous epoxy $C_9$ (From Example 17) | | | 100 | | |
| Epoxy 5 | | | | | 100 |
| Curing agent A | 22.2 | 24.5 | 20.8 | | 32 |
| Curing agent B | | | | 69.1 | |
| Catalyst B | 0.5 | 0.5 | 0.5 | 0.5 | 0.5 |
| Acetone | 0 | 0 | 0 | 22.5 | 0 |

TABLE 3

| | Examples 18-26 (Inventive) | | | | | | | | |
|---|---|---|---|---|---|---|---|---|---|
| Examples No. | 18 | 19 | 20 | 21 | 22 | 23 | 24 | 25 | 26 |
| Dk [1 MHz] | 4.54 | 4.69 | 4.71 | 4.45 | 4.56 | 4.62 | 4.5 | 4.50 | 4.55 |
| Df [1 MHz] | 0.013 | 0.010 | 0.012 | 0.011 | 0.015 | 0.013 | 0.011 | 0.013 | 0.010 |
| Peel strength (kgf/cm) | 1.8 | 1.9 | 1.9 | 1.8 | 1.7 | 1.8 | 1.9 | 1.8 | 1.9 |
| Water absorption (Wt %) | 0.24 | 0.26 | 0.25 | 0.28 | 0.21 | 0.26 | 0.20 | 0.16 | 0.15 |
| CTE $\alpha_1$(ppm) | 26.9 | 36.5 | 30 | 25.4 | 26.3 | 25.1 | 25.2 | 25.9 | 23.2 |
| CTE $\alpha_2$(ppm) | 232 | 260 | 245 | 219 | 230 | 235.0 | 215.6 | 221 | 210.5 |
| Tg | 137 | 123 | 150 | 145 | 141 | 129 | 150 | 156 | 140 |
| Td | 371 | 372 | 357 | 377 | 376 | 370 | 381 | 386 | 380 |
| Flame retardancy | V0 | V0 | V0 | V0 | V0 | V0 | V0 | V0 | V0 |
| Thermal stability S-288 (sec) | >180 | >180 | >180 | >180 | >180 | >180 | >180 | >180 | >180 |

TABLE 3a

| | Examples 27-31 (Comparative) | | | | |
|---|---|---|---|---|---|
| | Examples No. | | | | |
| | 27 | 28 | 29 | 30 | 31 |
| Dk [1 MHz] | 4.85 | 4.89 | 5.01 | 4.83 | 5.05 |
| Df [1 MHz] | 0.019 | 0.016 | 0.014 | 0.014 | 0.013 |
| Peel strength (kgf/cm) | 2.1 | 2.1 | 2.1 | 2.1 | 1.5 |
| Water absorption (Wt %) | 0.34 | 0.35 | 0.32 | 0.23 | 0.32 |
| CTE $\alpha_1$(ppm) | 40.6 | 47.4 | 39.2 | 34 | 32 |
| CTE $\alpha_2$(ppm) | 260.2 | 265.5 | 253 | 243 | 253 |
| Tg | 146 | 130 | 161 | 162 | 135 |
| Td | 371 | 373 | 350 | 380 | 367 |
| Flame retardancy | V0 | V0 | V0 | V0 | V0 |
| Thermal stability S-288 (sec) | >180 | >180 | >180 | >180 | >180 |

The data show that the inventive compositions provide excellent flame retardancy and thermal stability. Furthermore, based on the comparison above, the inventive compositions provide surprisingly better water resistance and dielectric properties than the comparative compositions.

The above embodiments are only used to illustrate the principle of the present disclosure and the effect thereof, and should not be construed as to limit the present disclosure. The above embodiments can be modified and altered by those skilled in the art, without departing from the spirit and scope of the present disclosure. Therefore, the protection scope of the present disclosure is defined in the following appended claims. As long as it does not affect the effects and achievable goals of this disclosure, it should be covered under the technical contents disclosed herein.

The terms "comprising," "having," and "including" are used in their open, non-limiting sense. The terms "a" and "the" are understood to encompass the plural as well as the singular. The expression "at least one" means one or more and thus includes individual components as well as mixtures/combinations. The term "about" when referring to a value, is meant specifically that a measurement can be rounded to the value using a standard convention for rounding numbers. For example, "about 1.5" is 1.45 to 1.54. All valued set forth herein can be modified with the term "about" or recited without the term, regardless of whether the term "about" is specifically set forth (or is absent) in conjunction with any particular value. All ranges and values disclosed herein are inclusive and combinable. For examples, any value or point described herein that falls within a range described herein can serve as a minimum or maximum value to derive a sub-range, etc.

The invention claimed is:

1. A compound of formula (I):

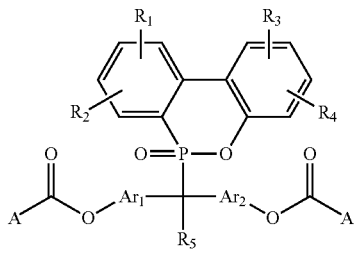

Formula (I)

wherein, $R_1$, $R_2$, $R_3$, and $R_4$ are independently selected from the group consisting of H, $C_1$-$C_{10}$ alkyl, $C_1$-$C_{10}$ alkoxy, and $C_3$-$C_{10}$ cycloalkyl;

$R_5$ is independently selected from the group consisting of $C_1$-$C_{10}$ alkyl, $C_1$-$C_{10}$ alkoxy, $C_3$-$C_{10}$ cycloalkyl, and $Ar_3$; and $Ar_1$ and $Ar_2$ are independently selected from the group consisting of

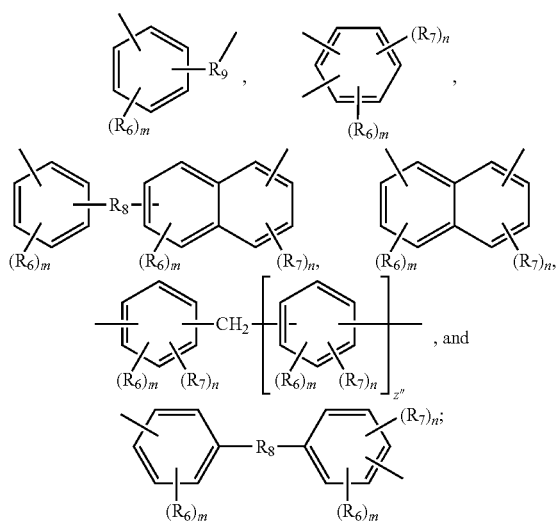

$Ar_3$ is selected from the group consisting of

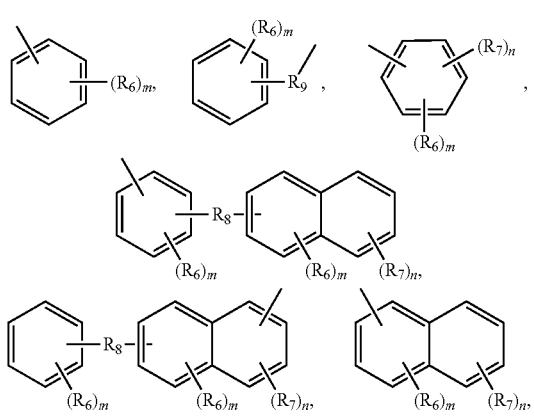

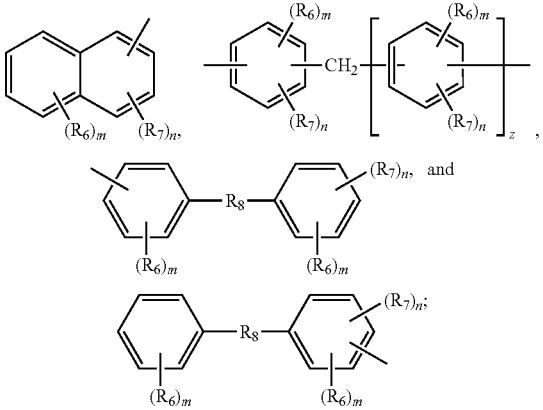

$R_6$ and $R_7$ are independently selected from the group consisting of H, $C_1$-$C_{10}$ alkyl group, $C_1$-$C_{10}$ alkoxy, and a cyclic alkyl group having 3-10 carbon atoms, m and n are independently an integer from 0 to 4;

$R_8$ is absent or is selected from the group consisting of —$CH_2$—, —$(CH_3)_2C$—, —CO—, —$SO_2$—, and —O—

$R_9$ is absent or is —$(CH_2)_p$—, wherein p is an integer from 1 to 20;

z is 1; and

A is selected from the group consisting of $C_1$-$C_{10}$ alkyl,

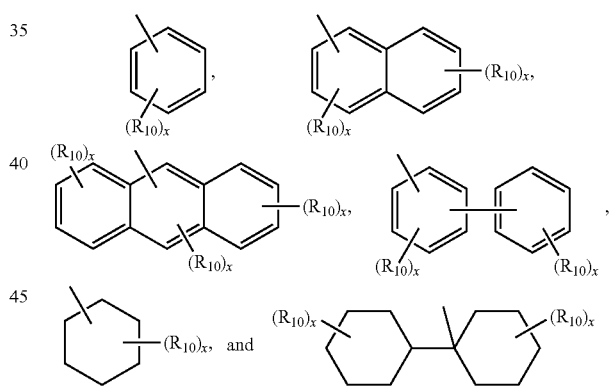

wherein, each $R_{10}$ is independently H or $C_1$-$C_{10}$ alkyl; and x is an integer from 0 to 4.

2. The compound of claim 1, wherein $R_5$ is $C_1$-$C_{10}$ alkyl.

3. The compound of claim 1, wherein $Ar_1$ and $Ar_2$ are

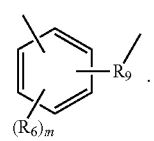

4. The compound of claim 3, wherein $R_9$ is absent.

5. The compound of claim 1, wherein $R_1$, $R_2$, $R_3$, and $R_4$ are hydrogen.

6. The compound of claim 1, wherein A is $C_1$-$C_{10}$ alkyl,

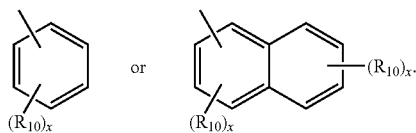

7. The compound of claim 6, wherein x is zero.

8. A flame retardant resinous composition comprising a compound of formula (I) as defined in claim 1 as a flame retardant.

9. A cured flame retardant resin prepared by cross-linking the flame retardant resinous composition of claim 8.

10. A compound of formula (Ia)

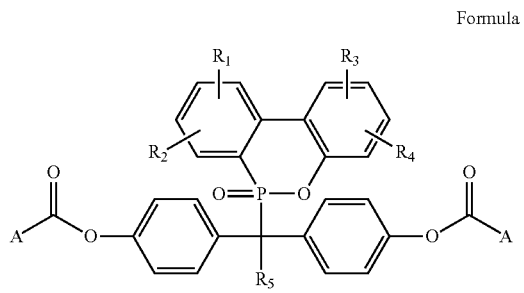

Formula (Ia)

wherein, $R_1$, $R_2$, $R_3$, and $R_4$ are independently selected from the group consisting of H, $C_1$-$C_{10}$ alkyl, $C_1$-$C_{10}$ alkoxy, and $C_3$-$C_{10}$ cycloalkyl;

$R_5$ is independently selected from the group consisting of $C_1$-$C_{10}$ alkyl, $C_1$-$C_{10}$ alkoxy, $C_3$-$C_{10}$ cycloalkyl, and $Ar_3$; and $Ar_3$ is independently selected from the group consisting of

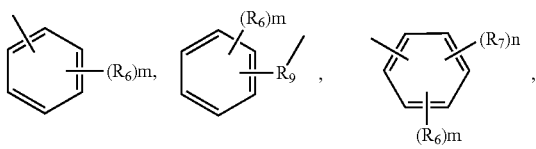

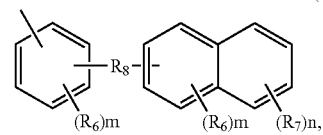

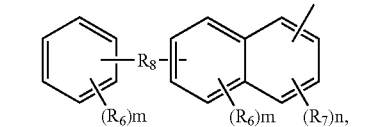

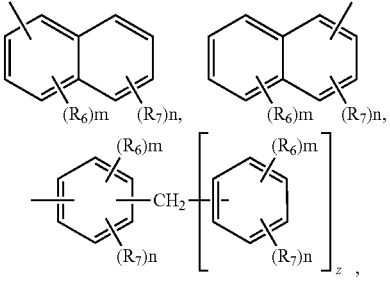

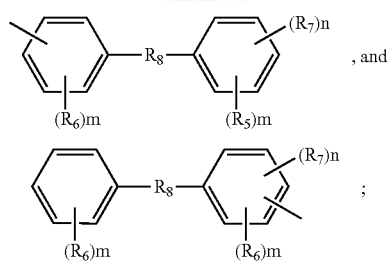

$R_6$ and $R_7$ are independently selected from the group consisting of H, $C_1$-$C_{10}$ alkyl group, $C_1$-$C_{10}$ alkoxy, and a cyclic alkyl group having 3-10 carbon atoms, m and n are independently an integer from 0 to 4;

$R_8$ is absent or is selected from the group consisting of —$CH_2$—, —$(CH_3)_2C$—, —CO—, —$SO_2$—, and —O—

$R_9$ is absent or is —$(CH_2)_p$—, wherein p is an integer from 1 to 20;

z is 1; and

A is selected from the group consisting of $C_1$-$C_{10}$ alkyl,

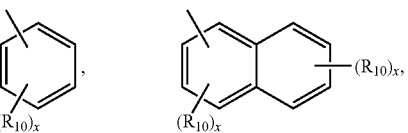

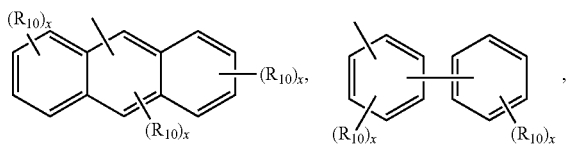

wherein, each $R_{10}$ is independently H or $C_1$-$C_{10}$ alkyl; and x is an integer from 0 to 4.

11. The compound of claim 10, wherein $R_5$ is $C_1$-$C_{10}$ alkyl.

12. The compound of claim 10, wherein $R_1$, $R_2$, $R_3$, and $R_4$ are hydrogen.

13. The compound of claim 10, wherein A is $C_1$-$C_{10}$ alkyl,

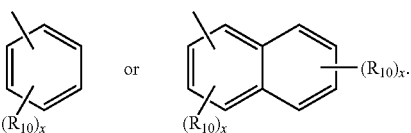

14. The compound of claim 13, wherein x is zero.

15. The compound of claim 10, wherein $R_5$ is methyl.

16. A compound of claim 10 selected from the group consisting of:

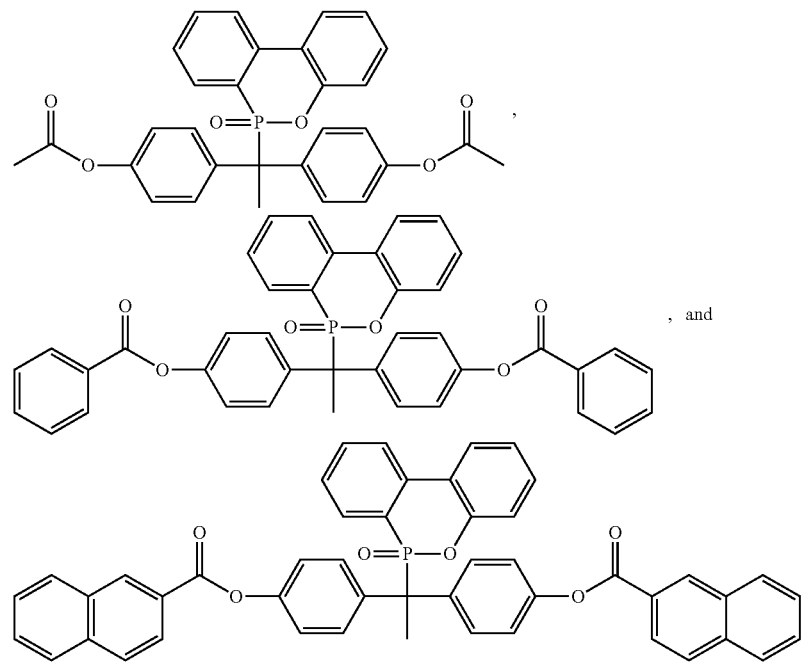
* * * * *

UNITED STATES PATENT AND TRADEMARK OFFICE
CERTIFICATE OF CORRECTION

PATENT NO. : 9,605,109 B1
APPLICATION NO. : 15/066745
DATED : March 28, 2017
INVENTOR(S) : An-Pang Tu et al.

Page 1 of 1

It is certified that error appears in the above-identified patent and that said Letters Patent is hereby corrected as shown below:

In Claim 1, Column 36, Line 5, the chemical structure:

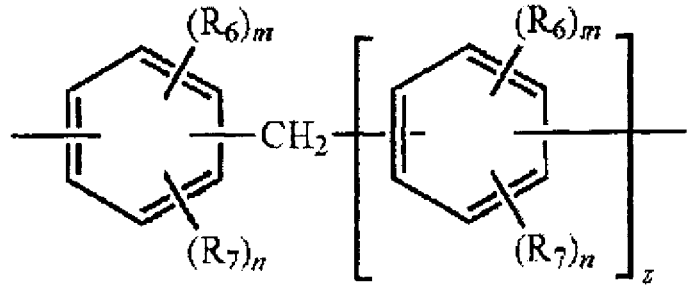

Should be:

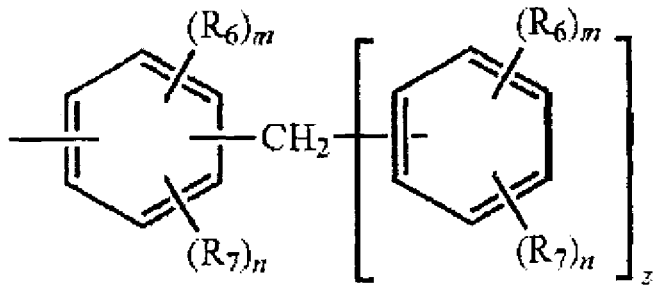

Signed and Sealed this
Twenty-fifth Day of July, 2017

Joseph Matal
*Performing the Functions and Duties of the
Under Secretary of Commerce for Intellectual Property and
Director of the United States Patent and Trademark Office*